US008395778B2

(12) United States Patent
Schumann et al.

(10) Patent No.: US 8,395,778 B2
(45) Date of Patent: Mar. 12, 2013

(54) SOOT NUMBER DETERMINING DEVICE AND METHOD FOR DETERMINING A SOOT NUMBER

(75) Inventors: Marcus Schumann, Lenzkirch (DE); Markus Grobert, Weilheim-Remetschwiel (DE); Patrick Schwoerer, Titisee-Neustadt (DE)

(73) Assignee: Testo AG, Lenzkirch (DE)

( * ) Notice: Subject to any disclaimer, the term of this patent is extended or adjusted under 35 U.S.C. 154(b) by 501 days.

(21) Appl. No.: 12/223,212

(22) PCT Filed: Jan. 25, 2007

(86) PCT No.: PCT/EP2007/000651
§ 371 (c)(1),
(2), (4) Date: Jun. 7, 2010

(87) PCT Pub. No.: WO2007/085460
PCT Pub. Date: Aug. 2, 2007

(65) Prior Publication Data

US 2010/0265508 A1 Oct. 21, 2010

(30) Foreign Application Priority Data

Jan. 26, 2006 (DE) ........................ 10 2006 003 734

(51) Int. Cl.
*G01N 21/00* (2006.01)

(52) U.S. Cl. ........................ 356/438; 356/437; 356/439

(58) Field of Classification Search .......... 356/436–438
See application file for complete search history.

(56) References Cited

U.S. PATENT DOCUMENTS

| | | | | |
|---|---|---|---|---|
| 2,058,073 | A | | 10/1936 | Fritzsching |
| 3,464,257 | A | | 9/1969 | Schreiber et al. |
| 3,653,773 | A | * | 4/1972 | Childs ........................ 356/432 |
| 3,903,727 | A | | 9/1975 | Sweet |
| 4,079,622 | A | | 3/1978 | Cocola et al. |
| 4,170,127 | A | | 10/1979 | Butera |
| RE31,232 | E | * | 5/1983 | Butera ........................ 73/23.33 |

FOREIGN PATENT DOCUMENTS

| | | | |
|---|---|---|---|
| AT | 267 232 | B | 12/1968 |
| AT | 348802 | | 6/1976 |
| DE | 28 34 642 | A1 | 8/1978 |
| DE | 3615111 | A1 | 5/1986 |

* cited by examiner

*Primary Examiner* — Michael P Stafira
(74) *Attorney, Agent, or Firm* — Muirhead and Saturnelli, LLC

(57) ABSTRACT

A soot number determining device has an intake line for taking in a soot-containing gas through a filter paper that has been introduced into the intake line. A transport apparatus transports a soot spot, which is produced at an intake position by virtue of the gas being taken in on the filter paper, by transporting the filter paper further to an evaluation position. A device is used to determine the extent of blackening of the filter paper.

33 Claims, 7 Drawing Sheets

SOOT NUMBER DETERMINING DEVICE AND METHOD FOR DETERMINING A SOOT NUMBER

TECHNICAL FIELD

This application relates to a soot number determining device. Such soot number determining devices are used to determine the soot number of a gas.

BACKGROUND OF THE INVENTION

To determine the soot number of a gas, a defined gas volume is usually drawn through a filter paper so that a soot spot remains on the paper. The blackening of the filter paper in the area of the soot spot depends in particular on the soot content of the gas. A so-called "soot number" is ascertained on the basis of the gray value of the soot spot as a measure of the soot content of the gas.

According to the Verordnung über Kleinfeuerungsanlagen (Erste Bundesimmissionsschutzverordnung vom 13. Februar 1996, Anlage III, Abschnitt: "Anforderungen an die Durchführung der Messung im Betrieb") [Regulations Governing Small Furnace Installations (First Federal Emission Prevention Regulations of Feb. 13, 1996, Appendix III, Section: "Requirements of Performing the Measurement During Operation"), one possibility of determining the blackening of the soot spot is by comparison with a gray value table. To this end, the filter paper is usually clamped in the intake line of the device and is then removed again after the soot spot has been created. Depending on the relevant specification, it may be necessary to perform several such measurements and to determine an average of the soot numbers determined on the basis of the individual measurements. However, use of such a device is very time-intensive because of the required insertion and removal of the filter paper. In addition, handling is made difficult due to the numerous individual elements because the soot number determining device must be set aside for the comparison of the withdrawn filter paper to the gray value table or it must be held in a nonergonomic manner. Furthermore, the soot number determined after each individual measurement is usually recorded by hand.

Therefore, it would be desirable to provide an inexpensive soot number determining device and a method by which a soot number may be easily determined and further processed.

SUMMARY OF THE INVENTION

A soot number determining device according to the system described herein includes an intake line using which a gas potentially containing soot is drawn through filter paper inserted into the intake line. A soot spot is thereby created on the filter paper in an intake position. The section of the filter paper on which the soot spot is located is then conveyed to an analysis position by a conveyor device (e.g., a stepping motor) operable manually or automatically.

For determining the soot number of the soot spot, a device for measuring the blackening of the filter paper is provided. This measurement may be performed either fully automatically with the help of a photodetector or manually and/or semiautomatically by comparison with a displaceable soot image reference scale.

For manual and/or semiautomatic determination of the soot number of the soot spot, a rotary or linearly displaceable soot image reference scale is provided, including a plurality of soot image reference areas. Each of the soot image reference areas has a predefined gray value and an opening. By rotating or displacing the soot image reference scale, the individual openings may be brought into the analysis position one after the other, so that the soot spot is visible through the particular opening.

The soot image reference scale is then rotated or shifted into a position which yields the best agreement between the gray value of the soot spot and the gray value of the soot image reference area in the analysis position.

As an alternative to rotation or displacement of the soot image reference scale, the filter paper may also be rotated and/or shifted with respect to the soot image reference scale. The deciding factor is only that the soot spot whose soot number is to be determined and each of the soot image reference areas are positionable relative to one another, so that a comparison of the gray value of the soot spot with the gray value of one of the soot image reference areas is possible by visual observation. The assigned soot value may then be determined on the basis of the position of the soot image reference scale with respect to the analysis position.

In fully automatic determination of the soot number with the help of a photodiode, the filter paper is illuminated, e.g., with the help of a light-emitting diode at a certain angle (angle of incidence) to the normal to the filter paper. The light reflected by the filter paper is measured with the help of a photodetector (e.g., a photodiode) at the same angle (angle of emergence=angle of incidence) symmetrically to the normal. The measurement principle here corresponds to that of a reflex optocoupler which is made up by the above-mentioned light-emitting diode and the photodiode, for example.

Accurate positioning of the filter paper relative to the reflex optocoupler is a special problem when using an optical measurement. In the optimal position, the soot spot on the filter paper, the light-emitting diode and the photodetector exactly form an equilateral triangle. This is referred to as the setpoint position of the soot spot. For the analysis, the filter paper having the soot spot is moved into an analysis position, which is just before the setpoint position. Next an entire measurement series of intensity values of the reflected light is recorded. The filter paper is moved away incrementally (in the direction of the setpoint position), one measurement being performed in each position. In each step, the soot spot comes closer to the setpoint position and the intensity of the reflected light declines. The setpoint position is reached when the intensity of the reflected light has reached a minimum. If the soot spot is moved further, the intensity of the reflected light increases again. The correct soot number is then determined from the minimum intensity value of the measurement series.

BRIEF DESCRIPTION OF THE DRAWINGS

The system described herein is explained in greater detail below on the basis of preferred exemplary embodiments with reference to the figures.

In the figures, the same reference numerals denote the same components having the same meanings.

DETAILED DESCRIPTION OF VARIOUS EMBODIMENTS

Figure 1A:
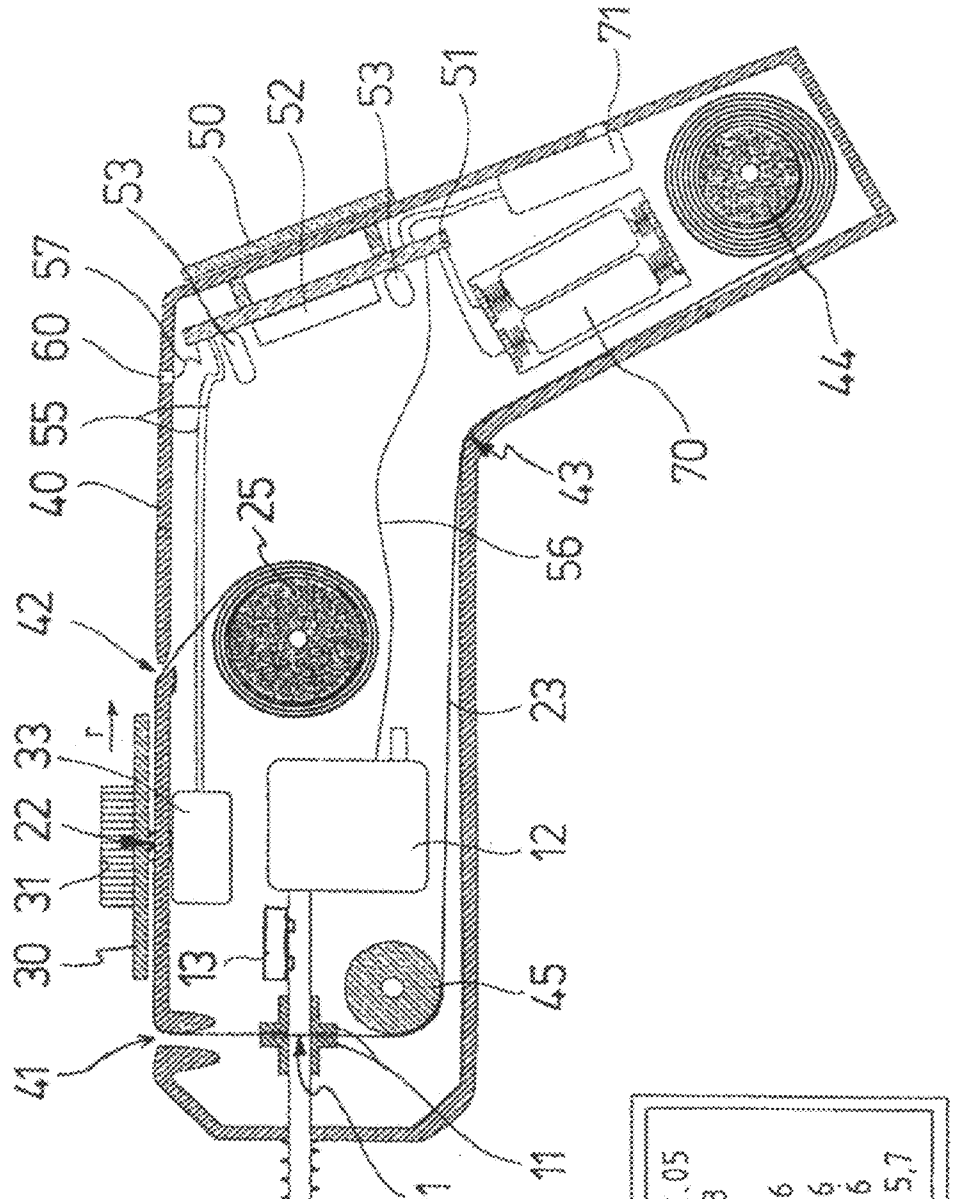
FIG. 1*a* shows a cross section through a soot number determining device according to an embodiment of the system described herein.

FIG. 1*a* shows a cross section through a soot number determining device according to an embodiment of the system described herein. The device has a preferably flexible intake line 10 for intake of a gas using an anti-kink spring 15. In deviation from the present representation, the intake line may also be designed to be removable from the device.

Intake line 10 may be inserted into an exhaust line, e.g., through a measurement opening. Intake of gas from the exhaust line is accomplished via an intake device 12 connected to intake line 10. Intake device 12 may be, for example, an electrically operated piston pump or diaphragm pump. Simpler embodiments of a soot number determining device may also have a manually operated intake device 12.

A filter paper 23 is inserted into intake line 10, so that the gas drawn in must pass through filter paper 23. If the gas drawn in contains soot particles, then a soot spot is formed in an area 21, where the gas passes through filter paper 23. This location in the area of the intake line is also referred to below as intake position 21.

A sealing device 11 is provided so that only the gas to be measured but no outside air is drawn in during the intake of the gas. Sealing device 11 may be designed as a screwed-on seal or as a clamped-on seal and is preferably operated electromechanically (via an electronic unit 51) or manually via a snap-on device.

Filter paper 23 may be clamped using two opposing flanges 11, for example. In doing so, filter paper 23 is first inserted between two flanges 11. These two flanges 11 are then pressed together, so that filter paper 23 is clamped between them in an essentially airtight manner.

To produce a soot spot, a defined quantity of gas to be measured, e.g., 1.63 L [STP]±0.7 L [STP] (L [STP]=liter at standard temperature and pressure) in the case of DIN 51402, is drawn in.

In the case of an electrically operated intake device 12, the intake volume may be determined, e.g., over a predefined running time of intake device 12. Likewise, in particular in the case of manually operated intake devices 12, e.g., a piston pump, it is possible to count the number of piston strokes and to calculate the total gas intake volume from the piston volume. Likewise, the intake volume may be adjusted using preferably a calorimetric flowmeter 13 or via a differential pressure measurement, e.g., based on the Venturi principle or the dynamic pressure principle.

The greater the amount of soot in the gas, the greater is the blackening of filter paper 23 by the soot spot in the area of the intake position, i.e., the darker is the soot spot thereby produced. For semiautomatic and/or manual analysis of the soot spot, the device for measuring the degree of blackening of filter paper 23 includes a gray scale, the degree of blackening of filter paper 23 being compared with the gray scale by direct comparison. This gray scale is referred to below as the soot image reference scale. To be able to compare the soot spot with the soot image reference areas of the soot image reference scale, sealing device 11 must first be slackened, so that the section of filter paper 23 provided with the soot spot may be conveyed out of intake position 21.

In an embodiment, filter paper 23 is designed as a strip and is rolled up onto a supply roll 44 situated in the handle of the soot number determining device. From there, it is supplied to intake position 21 via a paper guide 43, which is formed by a suitably shaped section of housing 40 and via deflecting roller 45. Filter paper 23 is then guided outward through a first opening 41 in housing 40 and runs preferably parallel to a section of housing 40 up to a second opening 42 of housing 40 through which it enters housing 40 again and is rolled up by a conveyor device 25.

Filter paper 23 may of course also remain in housing 40 in other embodiments (not shown) of a soot number determining device. However, in that case it is necessary to provide an opening or a window in housing 40 for observation of the soot spot to be measured.

Housing 40 has a rotary or displaceable soot image reference scale 30 beneath which filter paper 23 is passed. The rotary or displaceable soot image reference scale 30 is preferably situated on the outside of housing 40. As an alternative, rotary or displaceable soot image reference scale 30 may also be situated in the interior of the housing.

To be able to compare the gray value of the soot spot with soot image reference scale 30, the soot spot must be conveyed from intake position 21 into an analysis position 22.

Figure 2B:
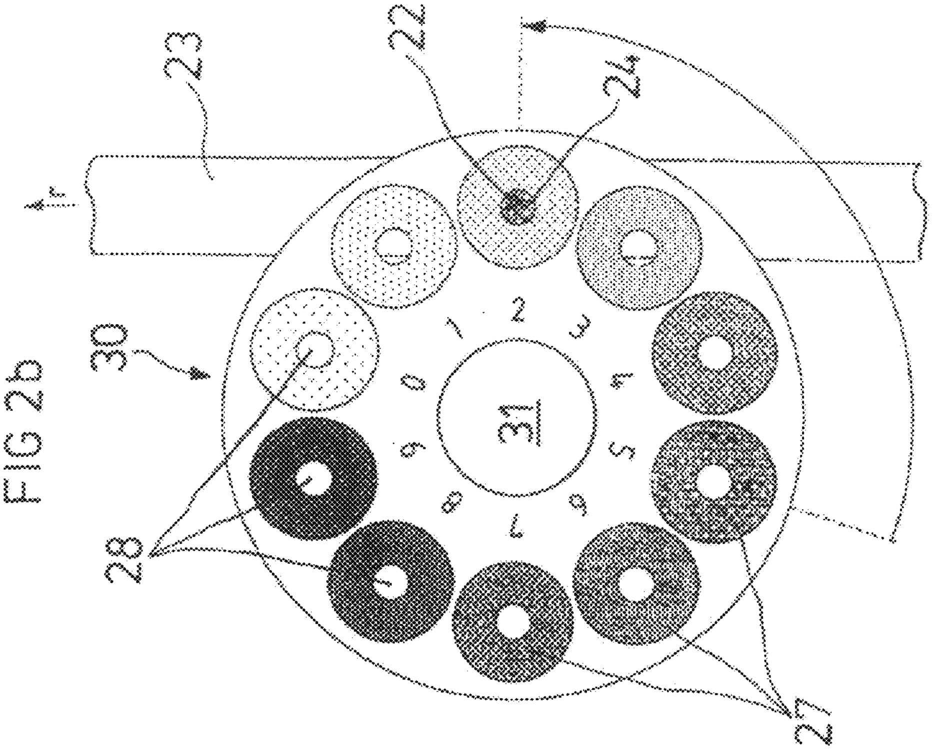
Figure 2A:
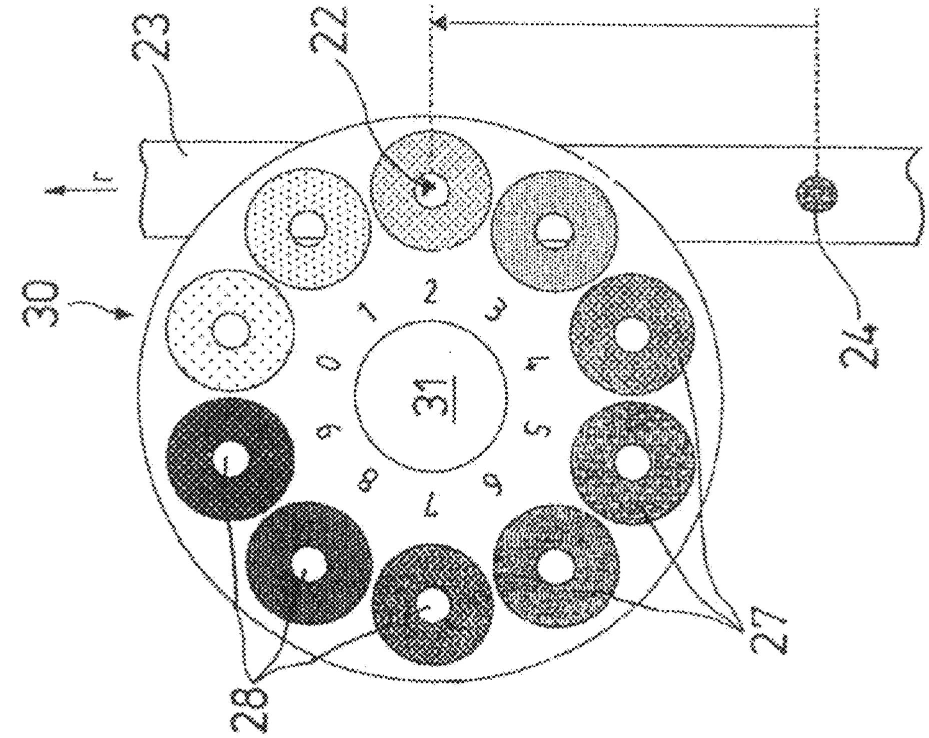

FIG. 2*a* shows a top view of soot image reference scale 30 and filter paper 23, which is passed beneath it. A representation of housing 40 according to FIG. 1*a* has been omitted here.

Soot image reference scale 30 includes a number of soot image reference areas 27, each having a different gray value. Soot image reference areas 27 are preferably circular in shape and have a diameter of approximately 20 mm, for example. Circular opening 28 having a diameter of 6 mm, for example, is situated at the center of each soot image reference area 27.

A “soot number” corresponding to the gray value of a particular soot image reference area 27 is assigned to each soot image reference area 27. In an embodiment, the soot image reference area having the lowest gray value is assigned a soot number of 0 and the soot image reference area having the highest gray value is assigned a soot number of 9. Filter paper 23 on which there is a spot 24 of soot is passed beneath soot image reference scale 30. For comparison of the gray value of soot spot 24, filter paper 23 is conveyed further in a direction of conveyance r, so that soot spot 24 is in an analysis position 22, as illustrated in FIG. 2*b*.

Analysis position 22 is defined with respect to housing 40 of the soot number determining device. Soot image reference areas 27 are arranged on soot image reference scale 30 in such a way that their openings 28 may be brought into analysis position 22 through an appropriate rotation of soot image reference scale 30, so that a soot spot 24 in analysis position 22 is visible through opening 28 and completely covers it when observed at a right angle. This allows a direct comparison between the gray value of soot spot 24 and the gray value of soot image reference area 27, which is in analysis position 22.

Figure 2C:
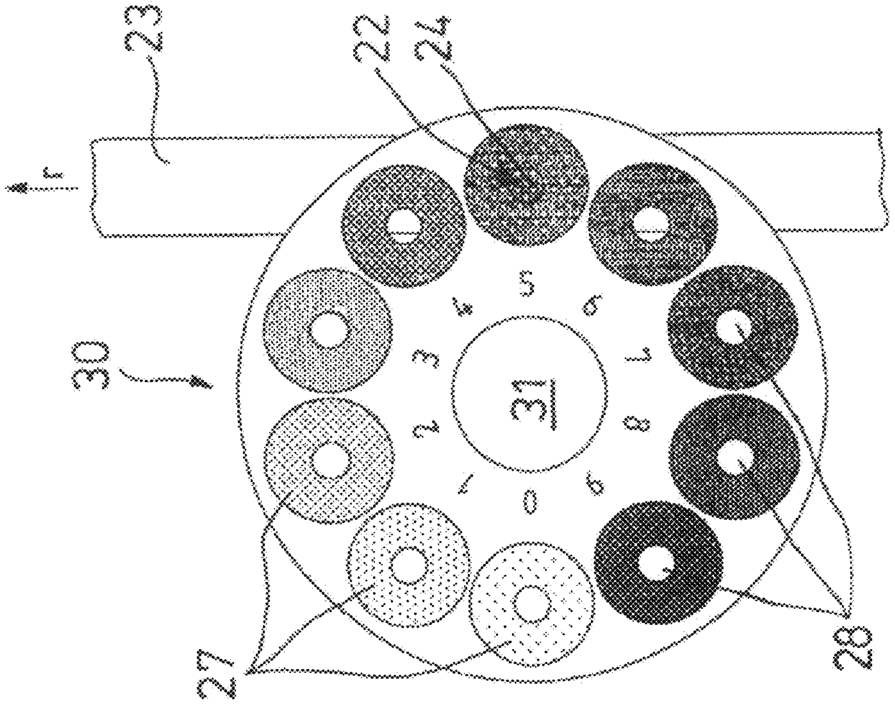

To determine the soot number to be assigned to soot spot 24, soot image reference scale 30 is rotated by rotation on its handle piece 31 until soot image reference area 27, whose gray value deviates the least from the gray value of soot spot 24, is in analysis position 22. Such a position is illustrated in FIG. 2*c*. The soot number assigned to soot spot 24 is then the soot number corresponding to soot image reference area 27, which is in analysis position 22. In the example according to FIG. 2*c*, soot spot 24 has a soot number of 5.

Figure 3:
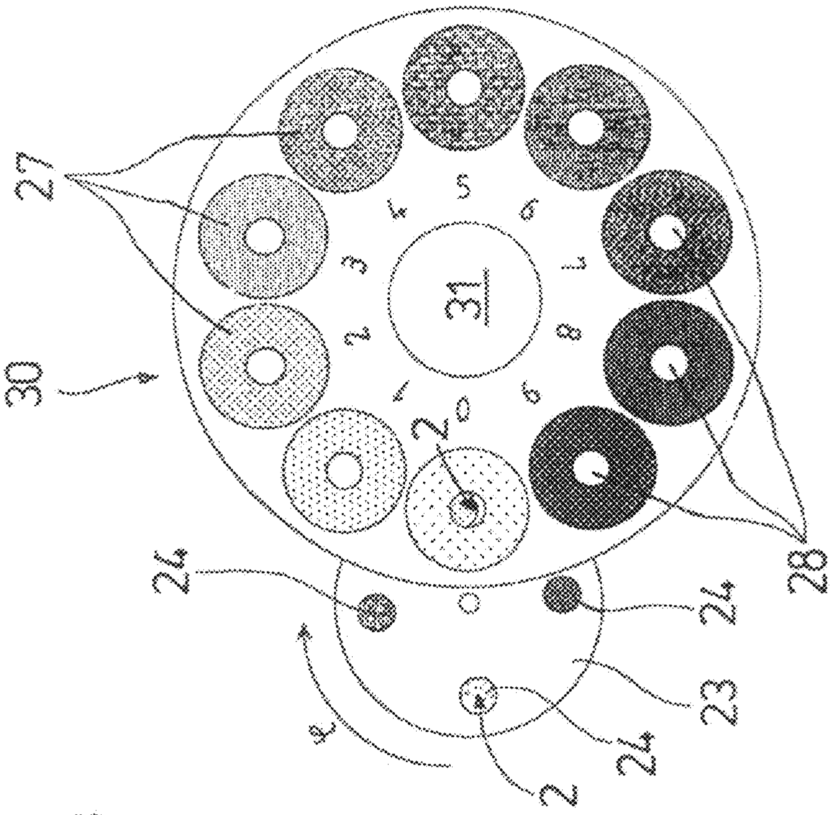
FIG. 3 shows a top view of a rotary soot image reference scale according to FIGS. 2*a* through 2*c*, beneath which a disk of filter paper provided with soot spots is situated, FIGS. 4*a* and *b* show views of a device for measuring the degree of blackening of filter paper used in connection with a soot number determining device according to an embodiment of the system described herein.

In the exemplary embodiments according to FIGS. 2*a* through 2*c*, filter paper 23 is designed as a strip. In principle, however, any other embodiments are also possible. FIG. 3 shows another exemplary embodiment in this regard. The design of soot image reference scale 30 corresponds to that according to FIGS. 2*a* through 2*c*. However, filter paper 23 is not designed as a filter paper strip as in FIGS. 1*a*, 2*a*-2*c* but instead is designed as a filter paper disk and is situated partially beneath soot image reference scale 30 in a plane parallel thereto.

By rotating filter paper 23 in a direction of rotation ϕ, a soot spot 24 created in an intake position 21 may be moved into an analysis position 22. The remaining procedure for determining the soot number of this soot spot 24 then takes place in the same way as described with reference to FIG. 2*c*.

As explained, the determined soot number for a certain soot spot 24 corresponds to the position of soot image reference scale 30 with respect to housing 40. This position may be analyzed electronically and processed further by visual comparison or through suitable measures.

FIG. 1*a* illustrates a device for determining a rotational position 33, namely in the present example a multiswitch to whose shaft soot image reference scale 30 is attached. Multiswitch 33 is connected via a connecting line 55 to an electronic unit 51, which includes a microcontroller 52 and other electronic components 53. Electronic unit 51 may include an electronic controller as well as an electronic analyzer, depending on which functions are needed in a certain soot number determining device.

After the user has brought soot image reference scale 30 into the position having the best agreement with the gray values, he may operate an input device (not shown), e.g., a button, to cause electronic unit 51 to determine the position of multiswitch 33 and, associated with this, the soot number assigned to soot spot 24. The position of multiswitch 33 and/or the soot number determined may then be stored, displayed on a display unit, or processed further in some other manner.

As an alternative or in addition to electronic analysis of the position of multiswitch 33, there is the possibility of determining the soot number of soot spot 24 by simply reading a soot number value corresponding to soot image reference area 27 of the best gray value agreement in a position of the soot image reference scale, which is in the position of the best agreement of the gray values. To do so, the corresponding soot number is preferably given in addition to each soot image reference area 27 of soot image reference scale 30.

Instead of a multiswitch, any other rotary encoders or linear position transmitters may be used for determining discrete, continuous or quasi-continuous rotational positions. For example, if a potentiometer is used in combination with a soot image reference scale having a continuous gray scale, then a continuous soot number may also be determined instead of a discrete soot number.

Optionally for comparison of the soot spot with the soot image reference scale, backlighting of the filter paper may be provided in the area of the soot spot to be analyzed. A device is optionally also provided for heating the measurement sites where the soot spot is created.

After the gray value of one or more soot spots has been determined, in an optional step the soot spot(s) may be tested for the presence of oil derivatives. To do so, a suitable solvent such as acetone is applied, preferably as a drop, to the soot spot. If this results in running in combination with a brownish discoloration of the filter paper, this is a sign that oil derivatives are present in the soot.

The solvent for the testing with regard to oil derivatives may be applied to the soot spot and to the filter paper manually, e.g., with a pipette, by operation of an operating element on the soot number determining device or automatically by an electronic unit of the soot number determining device.

Figure 4A:
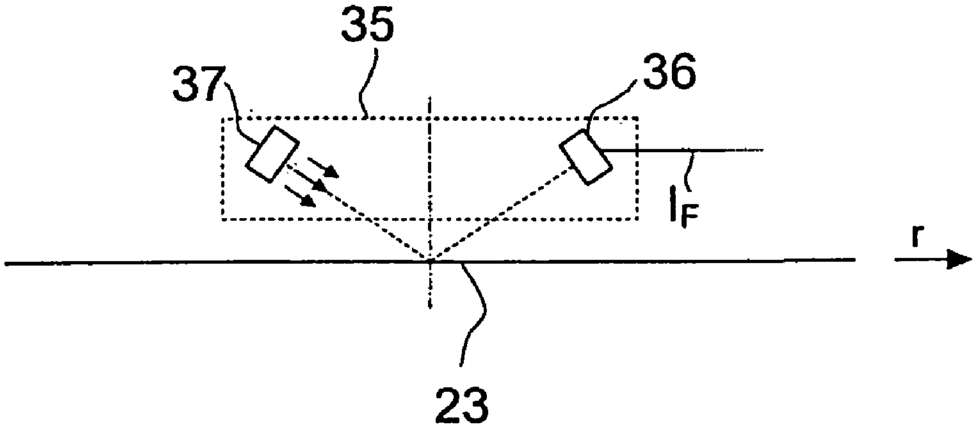
Figure 4B:
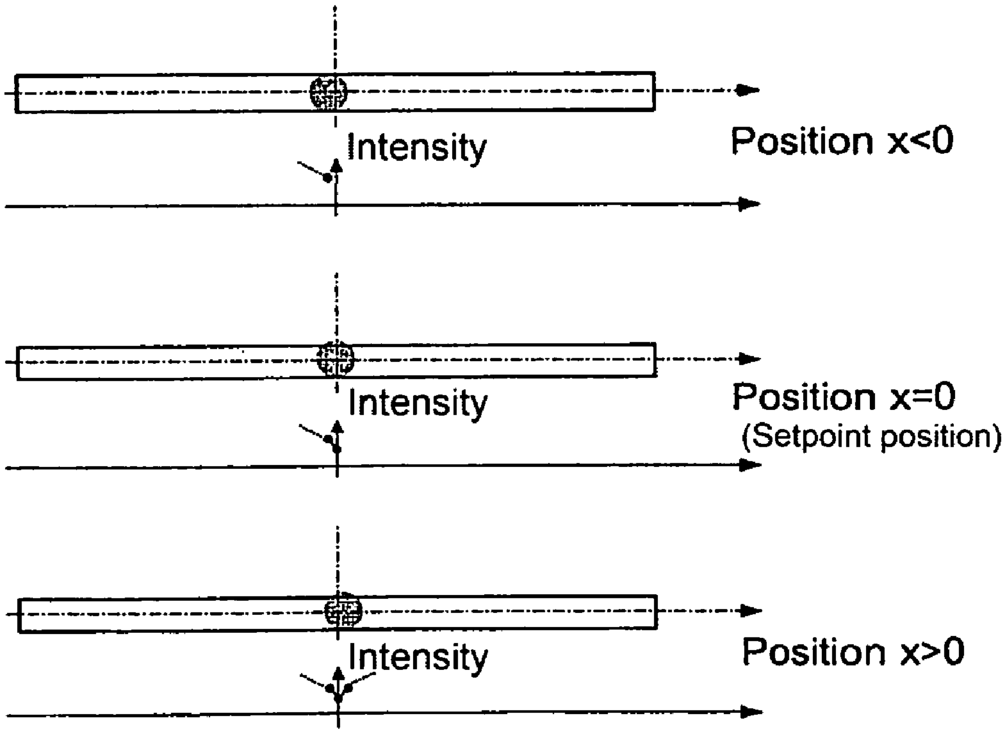

For fully automatic analysis of the soot spot, the device for measuring the degree of blackening of filter paper 23 includes, instead of a soot image reference scale 30, a light source 37 and a photodetector 36, which jointly form a reflex optocoupler 35. A corresponding exemplary embodiment is shown in FIGS. 4*a* and 4*b*. When there is only minor blackening (little soot) on filter paper 23, the amount of reflected light is great and the intensity measured by the photodiode is high. When there is a great deal of blackening (large amount of soot), only a small amount of the light is reflected and the rest is absorbed. The measured intensity is low.

According to the law of reflection (angle of incidence=angle of emergence), the soot spot must be positioned with the help of conveyor device 25, so that the light source (e.g., a light-emitting diode) illuminates the soot spot at a certain angle and the photodiode observes the soot spot at the same angle (symmetrical to the normal to filter paper 23). The photodiode, light source and soot spot must thus form an equilateral triangle, as diagrammed in FIG. 4*a*. This position is referred to below as the setpoint position.

Accurate positioning of the soot spot in relation to reflex optocoupler 35 is problematical with this exemplary embodiment because even minor mistakes in positioning may result in measurement errors that are not negligible. For this reason, section 21 of filter paper 23 having the soot spot is conveyed into an analysis position just in front of the setpoint position. In this exemplary embodiment, a stepping motor is very suitable for driving a conveyor device 25. The filter paper is then conveyed further in small increments until the soot spot comes to lie just after the setpoint position. After each of these increments, an intensity value of the reflected light is recorded with the help of photodetector 36, so that after the last step, an entire measurement series of intensity values is available. The measurement point of the measurement series having the lowest intensity value corresponds to the intensity value that was measured when the soot spot was in the setpoint position. This procedure is illustrated in FIG. 4*b*.

An accurate measurement of the position of the filter paper is thus superfluous. The intensity (and thus the degree of blackening) may nevertheless be measured with sufficient accuracy. Clearly it is not the intensity of the reflected light that is in fact measured but a photocurrent $I_F$ proportional thereto. The electric current measurement and the conversion to a soot number are performed in electronic unit 51, which is connected to the reflex optocoupler. Conveyor device 25 may also be triggered by electronic unit 51.

In certain applications, e.g., when a measurement according to DIN 51402 part 1 is required, multiple soot spots must be created, their particular soot number determined and from this an average soot number determined, which may likewise be performed by electronic unit 51 (in all the variants described above).

All the data compiled and/or ascertained by electronic unit 51 may be stored or processed in any other manner.

In particular a data interface 60, which is connected to electronic unit 51 via a connecting line 57, is provided for this purpose. Any interfaces may be used as data interface 60, but serial interfaces, preferably infrared interfaces (e.g., IrDA) or wireless interfaces (e.g., Bluetooth) are preferred. The relevant data, in particular the determined soot numbers, their averages, date, time and serial number of the soot number determining device may be transmitted via data interface 60 to a printer, a computer such as a PDA (personal data assistant) or to a flue gas analyzer, for example, and stored, printed out, displayed or otherwise processed further there.

A significant simplification for the user in operating the device is obtained when the soot spot created in intake position 21 is positioned correctly in analysis position 22 for performing the gray value comparison. This may be accomplished, for example, by conveyor device 25 conveying filter paper 23 by a predefined distance corresponding to the distance between intake position 21 and analysis position 22, measured along the paper path of filter paper 23.

The correct conveyance distance may be monitored, for example, by a measuring wheel, which is connected to electronic unit 51 and is also moved by conveyance of filter paper 23. The measuring wheel may be integrated into deflecting roller 45 shown in FIG. 1*a*, for example.

Conveyor device 25 and measuring wheel 45 are then preferably connected to electronic unit 51, so that the latter deactivates conveyor device 25 as soon as filter paper 23 has been conveyed further by the length of filter paper strip 23 required for proper placement of the soot spot created last at analysis position 22. To prevent slippage between the measuring wheel and filter paper strip 23, the latter may have a perforation in which the teeth of the measuring wheel engage.

For an electric power supply to the soot number determining device, use of one or more batteries or accumulators 70, preferably accommodated in the handle part of the device, is provided. In addition, a power pack 71, preferably designed as a switched-mode power supply, may also be provided for supplying the soot number determining device with power externally and optionally allowing its batteries 70 to be recharged.

For proper operation of the device, no outside air may be drawn in within the area of the sealing device. Therefore, flowmeter 13 or a pressure pickup (not shown) may be used, for example. Flowmeter 13 and/or the pressure pickup must therefore be connected to intake line 10 between intake position 21 and intake device 12.

To check for leaks, the end of intake line 10 is sealed airtight, the soot number determining device is switched to a test mode and intake device 12 is activated. If there is an influx of outside air in the area of sealing device 11, it may be detected by flowmeter 13 and/or by the pressure pickup of analysis and control electronic unit 51.

All determined values, in particular soot numbers, their averages, date, time, a serial number of the soot number determining device and battery status may be displayed on display unit 50, e.g., an LC display, as shown in FIG. 1*a*.

Figure 1B:
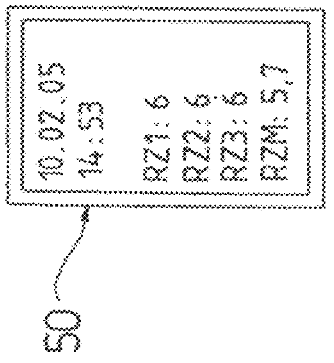
FIG. 1*b* shows a top view of the display unit of the soot number determining device according to FIG. 1*a*, FIGS. 2*a* through *c* show a top view of a rotary soot image reference scale beneath which a filter paper strip provided with a soot spot is passed.

FIG. 1*b* shows a top view of such a display unit 50, which shows, in addition to the date and time, three previously determined soot numbers "6," "6" and "5" (RZ1, RZ2, RZ3), as well as their average "5.7" (RZM) calculated by electronic unit 51 according to FIG. 1*b* and rounded to one place after the decimal.

Display unit 50 may also be used to display battery states such as the charge status of batteries 70, for displaying instructions, e.g., instructions for adjusting the soot image reference scale or for performing a leakage measurement or for display of other parameters.

With a soot number determining device according to the system described herein, in particular the shape of soot image reference scale 30, the shape, arrangement and number of soot image reference areas 27, the shape and arrangement of openings 28 in soot image reference areas 27 and the shape of filter paper 23 are not limited to the embodiments described here and their dimensions but may instead be adapted accordingly, depending on the intended purpose and, if necessary, any statutory standards associated therewith.

Figure 5:
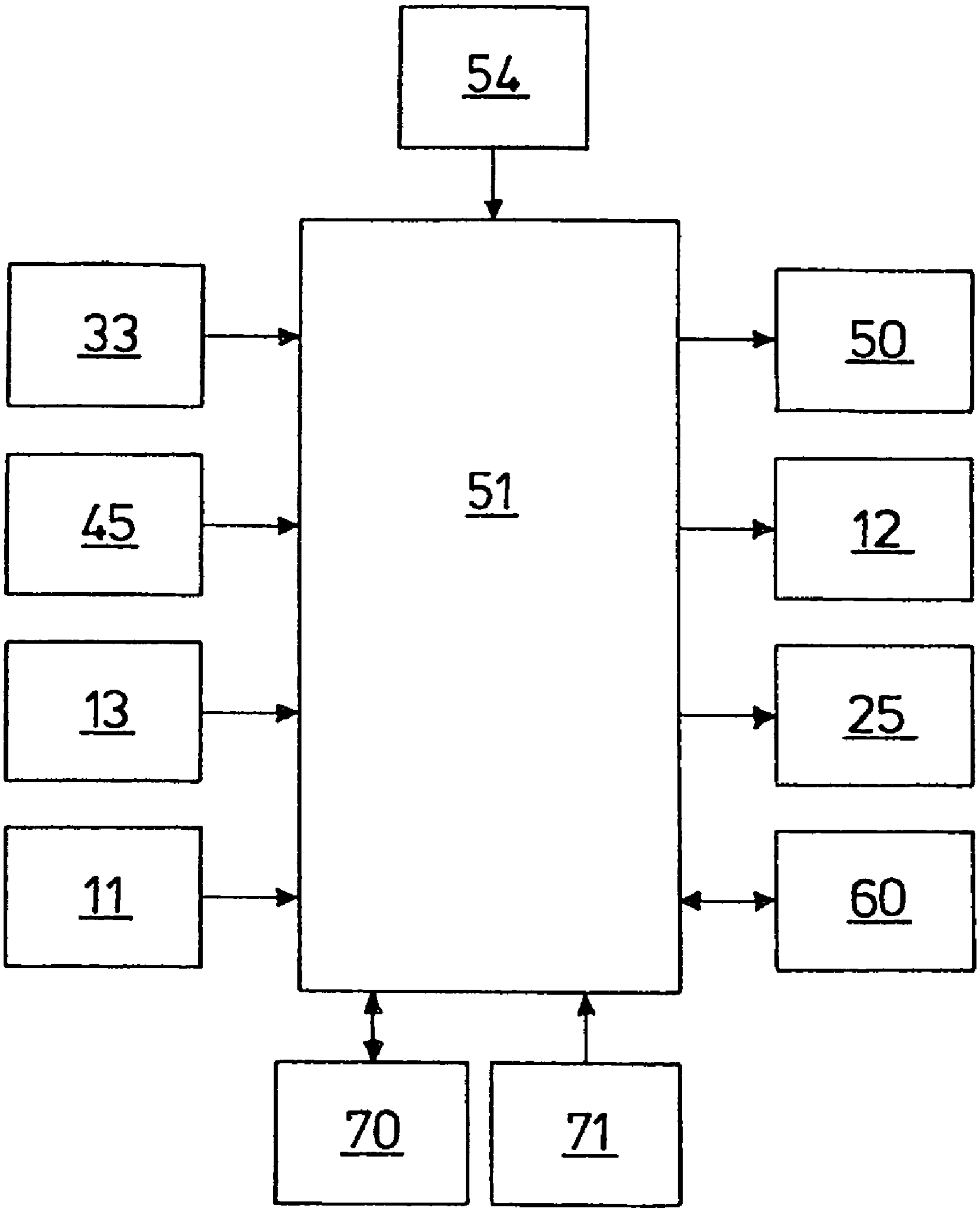
FIG. 5 shows a block diagram of a soot number determining device according to an embodiment of the system described herein.

FIG. 5 shows a block diagram of an exemplary soot number determining device. At the input end, a device 33 for determining the rotational position of a soot image reference scale 30, a sealing device 11, an intake device 12, a flowmeter 13, a measuring wheel 45 and an input device 54 are connected to an electronic unit 51, and at the output end a display unit 50, an intake device 12, a data interface 60 and a conveyor device 25 are connected. The power supply for electronic unit 51 is provided by batteries 70 and/or via a power pack having an optional charging function for batteries 70.

Based on a soot number determining device having a block diagram according to FIG. 5, a sequence of a soot number determination according to the system described herein is explained below in key points:

1. Turning on the soot number determining device;
2. Determining a first soot number for a first soot spot;
3. Determining a second soot number for a second soot spot;
4. Determining a third soot number for a third soot spot;
5. Testing the first soot spot for the presence of an oil derivative;
6. Testing the second soot spot for the presence of an oil derivative;
7. Testing the third soot spot for the presence of an oil derivative;
8. Determining the average of the first, second and third soot numbers;
9. Displaying the first, second and third soot numbers as well as the average and the date and time on display unit 50;
10. Storing the first, second and third soot numbers, the average, the date and time in electronic unit 51;
11. Providing the first, second and third soot numbers, the average, the date and time on data interface 60.

The sequence of steps listed above may be switched to any order, if technically feasible.

The second step (determination of a first soot number) and accordingly steps for determining additional soot numbers, such as steps 2 and 3, may have the following substeps in particular in the embodiment for semiautomatic and manual measurement (see FIGS. 1 and 2):

2.1 Closing sealing device 11;
2.2 Performing a leakage measurement;
2.3 Turning on intake device 12 for creating a soot spot 24;
2.4 Continuously determining the intake volume based on the signal of flowmeter 13, the running time of intake device 12 or the number of strokes of a piston of the intake device;
2.5 Turning off intake device 12 as soon as the intake volume has reached a predefined value;
2.6 Opening sealing device 11;
2.7 Further conveying filter paper 23 by activating conveyor device 25;
2.8 Continuously determining the transport distance of filter paper 23 by measuring wheel 45;
2.9 Deactivating conveyor device 25 as soon as the conveyance distance of filter paper 23 has reached a predefined value;
2.10 Manually adjusting soot image reference scale 30 depending on the gray value of soot spot 24; and
2.11 Operating of input device 54 to initiate the analysis of device 33 coupled to soot image reference scale 30 for determining the rotational position.

In the case of fully automatic optoelectronic measurement as explained in the description of FIG. 4, step 2 may include the following substeps:

2.1 Closing sealing device 11;

2.2 Performing a leakage measurement;

2.3 Activating intake device 12 to create a soot spot 24;

2.4 Continuously determining the intake volume based on the signal of flowmeter 13 or the running time of the intake device;

2.5 Deactivating intake device 12 as soon as the intake volume has reached a predefined level;

2.6 Opening sealing device 11;

2.7 Further conveying filter paper 23 by activation of conveyor device 25 to an analysis position beneath reflex optocoupler 35;

2.8 Recording a measurement series of intensity values by repeated incremental further conveyance of filter paper 23 with subsequent measurement of the intensity of the reflected light received by photodiode 36;

2.9 Determining the minimum intensity value of the measurement series;

2.10 Calculating the minimum soot number corresponding to the measured minimum intensity value.

Figure 6:
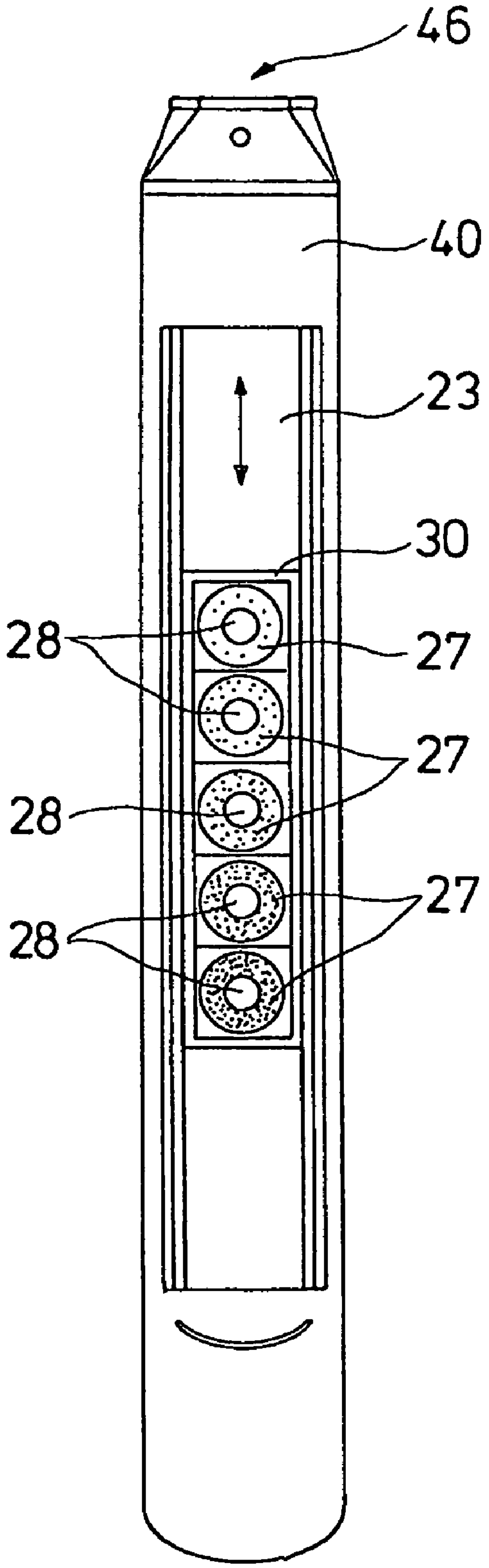
FIG. 6 shows a top view of another embodiment of a soot number determining device.

FIG. 6 shows another preferred embodiment of a soot number determining device. The soot number determining device has a linear soot image reference scale 30 running in the longitudinal direction of housing 40 and having five soot image reference areas 27. The number of soot image reference areas 27 is selected only as an example; it may essentially be adapted according to the application area and relevant specifications.

A strip of filter paper 23 runs beneath soot image reference scale 30, likewise in the longitudinal direction of housing 40.

Filter paper 23 and soot image reference scale 30 are displaceable with respect to each other. Either filter paper 23 is stationary with respect to housing 40 and soot image reference scale 30 may be displaceable with respect to housing 40, or conversely, soot image reference scale 30 may be stationary with respect to housing 40 and filter paper 23 may be displaceable with respect to housing 40.

For further electronic processing of the determined data, the positions of the soot image reference scale and/or filter paper may be determined electronically.

The embodiments already described on the basis of the soot number determining device according to FIG. 1*a* as well as the other figures may also be applied to the soot number determining device according to FIG. 6.

Figure 7:
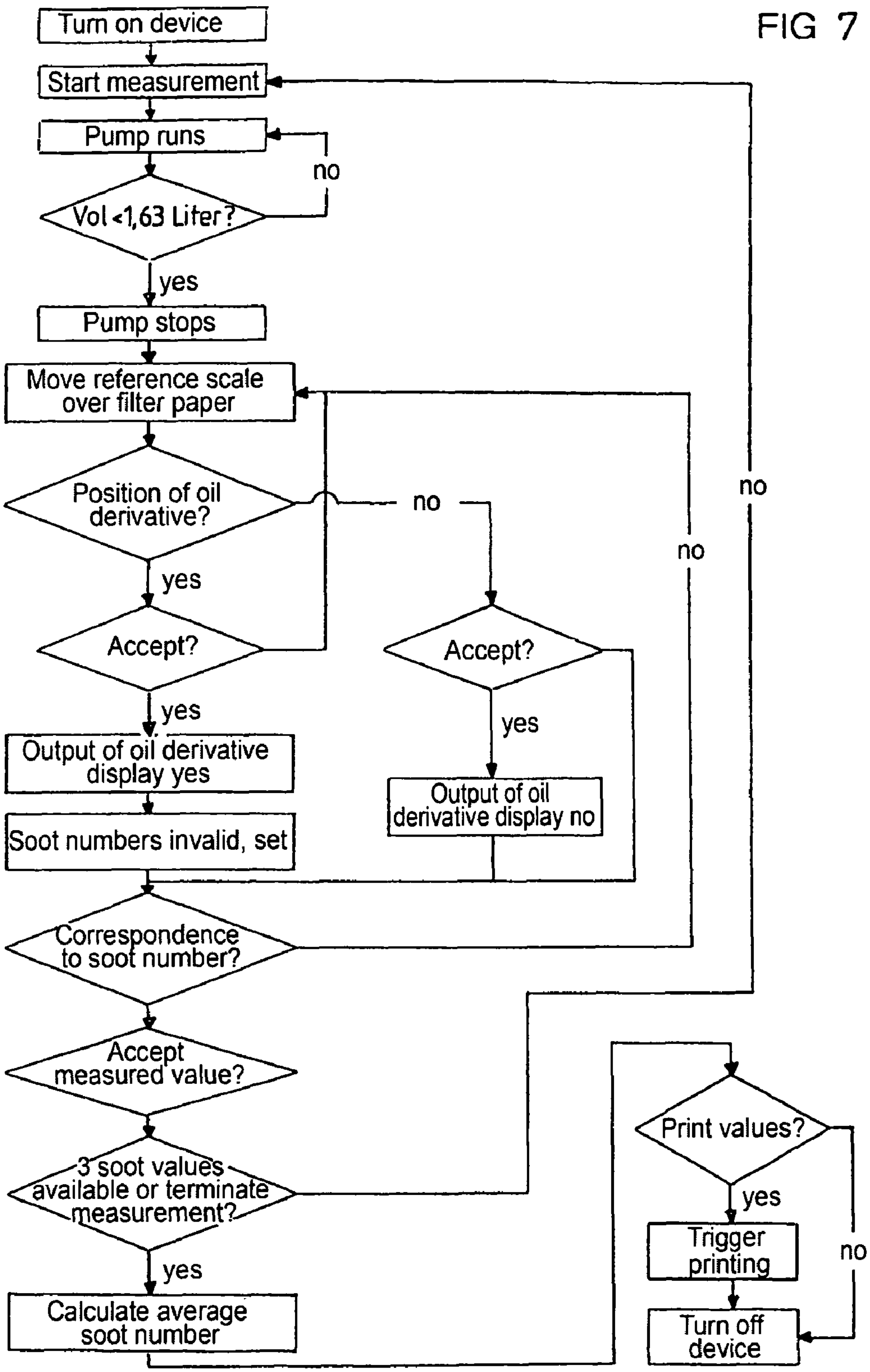
FIG. 7 shows a flow chart for operation of a soot number determining device according to an embodiment of the system described herein.

FIG. 7 shows a flow chart for operation of a soot number determining device according to an embodiment of the system described herein.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A soot number determining device, comprising:

an intake line for intake of a gas potentially containing soot through a filter paper introduced into the intake line;

a conveyor device that conveys a soot spot created on the filter paper by intake of the gas at an intake position into an analysis position; and a device for measuring the degree of blackening of the filter paper caused by the soot spot, wherein the device includes at least one of:

(i) a reflex optocoupler having a light source and a photodetector, the soot spot being conveyed into the analysis position in front of a setpoint position, the filter paper then being conveyed further in increments until the soot spots lies after the setpoint position, wherein the reflex optocoupler records measurements of an intensity value of reflected light from the soot spot, and the soot number being determined from a minimum of a measurement series on which the measurements are performed; or (ii) a soot image reference scale having a plurality of soot image reference areas, each of which has a predefined gray value and an opening, wherein each opening of the soot image reference scale is positionable with respect to the soot spot of into the analysis position so that the soot spot is visible through the opening, the soot image reference scale being coupled to a position transmitter for determining a position with respect to the analysis position.

2. The soot number determining device as recited in claim 1, wherein the photodetector is connected to an electronic unit.

3. The soot number determining device as recited in claim 2, wherein the electronic unit measures a photoelectric current provided by the photodetector.

4. The soot number determining device as recited in claim 1, wherein the soot image reference scale is rotary or displaceable.

5. The soot number determining device as recited in claim 1, wherein the position transmitter is connected to an electronic unit.

6. The soot number determining device as recited in claim 2, wherein the electronic unit determines the soot number.

7. The soot number determining device as recited in claim 6, wherein the electronic unit determines an average soot number from a plurality of soot numbers.

8. The soot number determining device as recited in claim 2, further comprising:

a display unit which is connected to the electronic unit.

9. The soot number determining device as recited in claim 1, wherein the filter paper is a strip of filter paper.

10. The soot number determining device as recited in claim 9, further comprising:

a filter paper supply roll that supplies the filter paper.

11. The soot number determining device as recited in claim 1, wherein the conveyor device is a winding device.

12. The soot number determining device as recited in claim 1, further comprising:

a measuring wheel for determining a filter paper conveyance distance.

13. The soot number determining device as recited in claim 12, wherein the measuring wheel is connected to an electronic unit.

14. The soot number determining device as recited in claim 12, wherein the measuring wheel has teeth which engage in a perforation of a strip of the filter paper inserted into the soot number determining device.

15. The soot number determining device as recited in claim 1, wherein the filter paper is a filter sheet.

16. The soot number determining device as recited in claim 1, wherein the intake device is an electric suction pump.

17. The soot number determining device as recited in claim 1, wherein the intake device is connected to an electronic unit.

18. The soot number determining device as recited in claim 1, further comprising:

a data interface.

19. The soot number determining device as recited in claim 1, wherein the conveyor device is controllable depending on a rotary encoder mechanically coupled to the filter paper.

20. The soot number determining device as recited in claim 1, wherein the conveyor device includes a stepping motor.

21. A method for determining the soot number of a gas potentially containing soot, comprising:

providing a soot number determining device, wherein the soot number determining device includes:

an intake line for intake of a gas potentially containing soot through a filter paper introduced into the intake line;

a conveyor device that conveys a soot spot created on the filter paper by intake of the gas at an intake position into an analysis position; and a device for measuring the degree of blackening of the filter paper caused by the soot spot;

positioning a section of the filter paper in the intake position, which is in the intake line;

intaking a predefined volume of the gas via an intake device pneumatically connected to the intake line, so that when soot is present, a soot spot is created on the section of the filter paper;

conveying the section of the filter paper from the intake position into an analysis position beneath the device for measuring the degree of blackening; and measuring the degree of blackening of the filter paper and determining the soot number as a function of the measured degree of blackening;

and the method further comprising at least one of:

(i) positioning the section of the filter paper from the intake position into the analysis position beneath a reflex light barrier, then determining a measurement series of intensity values of light reflected on the section of the filter paper, the filter paper being conveyed further between each measurement point of the measurement series with the help of the conveyor device and then determining the soot number from a minimum of the measurement series; or (ii) conveying the section of the filter paper from the intake position into the analysis position beneath a soot image reference scale including a plurality of soot image reference areas, and positioning the soot image reference scale in a rotational position in which the particular soot image reference area whose gray value differs the least from the gray value of the soot spot of is positioned in the analysis position, and then determining the soot number as a function of the rotational position of the soot image reference scale with respect to the analysis position.

22. The method as recited in claim 21, wherein the soot image reference scale is positioned by at least one of: rotation or displacement of the soot image reference scale.

23. The method as recited in claim 21, wherein the soot number is determined as a function of the rotational position of the soot image reference scale with respect to the analysis position via a rotary encoder, which is coupled to the soot image reference scale.

24. The method as recited in claim 21, wherein the soot number is a first soot number, and further comprising:

determining at least one second soot number; and determining an average soot number which is determined from the first soot number and the at least one second soot number.

25. A method for determining the soot number of a gas, comprising:

positioning filter paper in an intake position, wherein the gas flows through the intake position;

intaking a volume of the gas through the filter paper, wherein a soot spot is created on the filter paper;

conveying the filter paper from the intake position into an analysis position;

measuring a degree of blackening of the soot spot on the filter paper in the analysis position; and determining the soot number as a function of the measured degree of blackening, wherein measuring the degree of blackening or determining the soot number includes at least one of:

(i) using a light source and a photodetector, the soot spot being conveyed into an analysis position in front of a setpoint position, the filter paper then being conveyed further in small increments until the soot spot lies after the setpoint position, recording measurements of an intensity value of the reflected light, and determining the soot number from a minimum of a measurement series on which the measurements are performed, or (ii) using a soot image reference scale having a plurality of soot image reference areas, each of which has a predefined gray value and an opening wherein each opening of the soot image reference scale is positionable with respect to the soot spot into an analysis position so that the soot spot is visible through the opening, wherein the soot image reference scale is coupled to position transmitter for determining a position with respect to the analysis position.

26. The method according to claim 25, wherein the method includes using the soot image reference scale of the step (ii).

27. The method according to claim 25, wherein the method includes using the light source and the photodetector of the step (i).

28. The soot number determining device according to claim 1, wherein the device includes the soot image reference scale of the feature (ii).

29. The soot number determining device according to claim 1, wherein the device includes the reflex optocoupler of the feature (i).

30. The method according to claim 21, wherein the method includes using the soot image reference scale of the step (ii).

31. The method according to claim 21, wherein the method includes using the light source and the photodetector of the step (i).

32. A soot number determining device, comprising:

an intake line for intake of a gas potentially containing soot through a filter paper introduced into the intake line;

a conveyor device that conveys a soot spot created on the filter paper by intake of the gas at an intake position into an analysis position; and a device for measuring the degree of blackening of the filter paper caused by the soot spot, wherein the device includes a soot image reference scale having a plurality of soot image reference areas, each of which has a predefined gray value and an opening, wherein each opening of the soot image reference scale is positionable with respect to the soot spot into the analysis position so that the soot spot is visible through the opening, wherein the soot image reference scale is coupled to a position transmitter for determining a position with respect to the analysis position, and wherein the position transmitter is connected to an electronic unit.

33. A method for determining the soot number of a gas potentially containing soot, comprising:

providing a soot number determining device, wherein the soot number determining device includes:

an intake line for intake of a gas potentially containing soot through a filter paper introduced into the intake line;

a conveyor device that conveys a soot spot created on the filter paper by intake of the gas at an intake position into an analysis position; and a device for measuring the degree of blackening of the filter paper caused by the soot spot;

positioning a section of the filter paper in the intake position, which is in the intake line;

intaking a predefined volume of the gas via an intake device pneumatically connected to the intake line, so that when soot is present, a soot spot is created on the section of the filter paper;

conveying the section of the filter paper from the intake position into an analysis position beneath the device for measuring the degree of blackening; and measuring the degree of blackening of the filter paper and determining the soot number as a function of the measured degree of blackening, wherein the soot number is a first soot number, and wherein the method further comprises determining at least one second soot number; and determining an average soot number which is determined from the first soot number and the at least one second soot number.

* * * * *